United States Patent

Bravomalo

(10) Patent No.: US 6,643,385 B1
(45) Date of Patent: Nov. 4, 2003

(54) SYSTEM AND METHOD FOR WEIGHT-LOSS GOAL VISUALIZATION AND PLANNING AND BUSINESS METHOD FOR USE THEREFOR

(76) Inventor: Mario J. Bravomalo, 2315 Eagle Park, Arlington, TX (US) 76001

( * ) Notice: Subject to any disclaimer, the term of this patent is extended or adjusted under 35 U.S.C. 154(b) by 0 days.

(21) Appl. No.: 09/560,243

(22) Filed: Apr. 27, 2000

(51) Int. Cl.⁷ .................................................. G06T 3/00
(52) U.S. Cl. ...................... 382/100; 382/293; 345/646; 348/77; 396/14; 705/10
(58) Field of Search .................................. 382/100, 276, 382/277, 293; 345/646, 647; 348/77; 396/14; 705/10

(56) References Cited

U.S. PATENT DOCUMENTS

| | | | |
|---|---|---|---|
| 4,602,280 A | * 7/1986 | Maloomian | .................. 382/100 |
| 5,687,259 A | 11/1997 | Linford | |
| 5,825,941 A | 10/1998 | Linford | |
| 5,854,850 A | 12/1998 | Linford | |
| 5,963,214 A | 10/1999 | Cok | |
| 5,982,949 A | 11/1999 | Ohtsuka | |
| 5,986,671 A | 11/1999 | Fredlund | |
| 6,095,949 A | * 8/2000 | Arai | .............................. 482/4 |
| 6,336,136 B1 | * 1/2002 | Harris | ......................... 709/219 |
| 6,348,923 B2 | * 2/2002 | Murata | ......................... 345/629 |

OTHER PUBLICATIONS

Efit, Efit MorphOver, Apr. 10, 2000, pp. 1–2, http://www./efit.com/morphover/.

Sound Feelings, Slim Photo Fitness Motivation Tool, Apr. 10, 2000, pp. 1–4, http://www.soundfeelings...native_medicine/weight_loss/fitness.htm.

* cited by examiner

*Primary Examiner*—Jon Chang
(74) *Attorney, Agent, or Firm*—Robert H. Frantz

(57) ABSTRACT

The visual fitness planner combines image morphing technology, exercise programming, supplement sales, and motivational techniques; into one product. Users begin by entering their current measurements, measurement goals and current picture into the system, preferably via a Web site. The picture is segmented into body components, and each segment is morphed based upon the goal measurement and the segment's responsiveness to weight loss using physiological tables and formulae. The resulting modified "after view"image is then returned to the user, preferably by online communications such as e-mail. In the business use for the disclosed system, the visual fitness planner helps the fitness industry overcome two of their biggest problems: obtaining new members and retaining current members. By showing members how they will look after following a specific regimen, client may accurately visualize their future appearance, resulting in increased client loyalty and satisfaction.

30 Claims, 6 Drawing Sheets

SYSTEM AND METHOD FOR WEIGHT-LOSS GOAL VISUALIZATION AND PLANNING AND BUSINESS METHOD FOR USE THEREFOR

TECHNICAL FIELD OF THE INVENTION

This invention relates to the arts of visual image processing to predict a subject's appearance after a given amount of weight loss. This invention relates to the business methods employing a predictive image visualization system to attract and retain clients of service provides in the weight loss food program, fitness center, physical therapy and sports medicine, and weight control medical industries.

CROSS-REFERENCE TO RELATED APPLICATIONS

Not applicable.

FEDERALLY SPONSORED RESEARCH AND DEVELOPMENT STATEMENT

This invention was not developed in conjunction with any Federally-sponsored contract.

MICROFICHE APPENDIX

Not applicable.

BACKGROUND OF THE INVENTION

Many people desire to decrease their body weight, especially their body fat content Modem life styles include highly sedentary weekday routines such as computer-based desk jobs, low-exercise commuting routines such as transportation by private automobile, coupled with high-fat, high-calorie food choices often eaten quickly or while "on the run". Besides genetic tendencies, these factors lead many people to be dissatisfied with their appearance.

The problem is so prevalent that billion dollar industries have evolved to help people overcome their body dissatisfaction, including packaged food programs such as Weight Watchers (TM) and Jenny Craig (TM), fitness and workout centers such as Bally's (TM), and physical therapy and sports medicine centers. This industry has also attracted medical and osteopathic doctors to specialize in use the use of diet, exercise, and sometimes prescriptive regimens to help their clients and patients achieve their weight and appearance goals.

According to marketLooks.com (TM), there are currently over 24,000 health clubs in the United States with 40 million members generating over 12 billion dollars in revenue each year. In 1995, health clubs and private individuals spent 3.2 billion dollars on fitness equipment alone, and these revenues are expected to reach 4.9 billion, a 38% increase by the year 2001. In 1996, $500 million was spent on meal replacements and protein drinks, and these sales are expected to grow by 30% over the next five years.

However, many people fail to meet their goals, despite their efforts and the amounts they spend. The two most common reasons people fail in their attempt to change their body weight and appearance are lack of understanding and motivation.

Client and Patient Education

Previous technologies, systems and methods do not adequately provide for the education and understanding of how exercise and diet affect the physiology of a person, especially taking into consideration of the person's frame size or "build" and metabolism. Some available technologies include the ability to scan a photograph or import an image from a digital camera of a client or patient, and to digitally alter the image manually to produce an estimate of the client's future appearance.

Currently available systems and methods simply "shrink" an image, such as by hand manipulation and editing of a digitized photograph, also known as digital "retouching". However, different body builds will store fat in different amounts in various portions of the body, and different exercises will reduce and/or firm up different body areas unevenly. Additionally, certain features of the body will show little or no response to weight change. For example, if the width of an image of a leg is decreased by a certain percentage, the appearance of the knee will be changed. However, knees generally do not have a significant fat layer, and thus represent a minimum circumference at almost any weight. So, the resulting image would predict an overall thin appearance to a leg which is not physiologically achievable. Similar factors apply to other points in the body, such as the width of shoulders and hips, and circumference of joints. As this method is highly inaccurate, it does not provide the level of education a client or patient needs to understand why particular diet and exercises have been recommended, and how to adjust and apply this information in the future.

In order to accurately predict a future appearance, many physiological factors must be taken into account with diet and exercise goals. Estimating the results of these changes is typically beyond the technical and medical education and skill sets of most staffers at weight loss packaged food program outlets and physical fitness centers, and may be highly labor intensive and expensive to generate by appropriately qualified health and medical professionals.

At present, there are a few resources available on the Internet. One service, called MorphOver (TM) from eFit of New York City, N.Y., provides a service in which users e-mail a digital photograph in JPEG format to their website without any body measurements, body fat data, or indicated goals, and the service returns a "slimmed" photograph file within a few weeks. The instructions indicate that the original or "before" photograph must be of the subject in dark clothing, in a certain position, and with a white background. Another on-line service, this one offered by Sound Feelings Publishing of Reseda, Calif., is similar in that it only requires submission of a photograph without any data as to the subject's body fat, dimensions, or goals. Additionally, the advertisement for this service states that a digital photograph artist will spend at least two hours manually manipulating the photograph.

Client and Patient Motivation

There are very few credible, non-surgical remedies for rapid weight loss. Therefore, successful weight-loss programs require months to even years of commitment and adherence to diet and exercise regimens prescribed. If a client or patient becomes unmotivated or loses confidence a program, he or she will not continue the program. Further, this client or patient may have negative effects to the attraction and retention of other clients and patients as they will report to their friends and acquaintances that the program is another "scam" or "doesn't work", or that a particular professional is not competent. This can lead to a decline in memberships of businesses which are membership-based.

Therefore, there is a need in the art for a visual fitness planner which accurately produces predicted images of a weight-loss client or patient. There also exists a need in the art for this visual fitness planner system and method to be operable by persons of usual skill and education who are commonly employed in the package food program and fitness center industries. Further, there is a need in the art for this visual fitness planner to easily and quickly produce intermediate images, such as weekly or monthly predictions, in order to provide accurate and positive confidence reinforcement to the client or patient, thereby enhancing the likelihood that the client or patient will continue to abide by the program and ultimately achieve his or her goals. There also exists a need in the art for this visual fitness planner to be realizable both in a networked or Internet-based form, or in a single workstation form. Additionally, there exists a need in the art for a method of leveraging a visual fitness planner to attract and retain clients and patients in this industry.

SUMMARY OF THE INVENTION

System Overview

The Visual Fitness Planner is an Internet fitness profiler which helps users gain insight into their fitness plan and projected outcome and results. The Visual Fitness Planner combines image morphing technology, exercise programming, supplement sales, and motivational techniques into one product.

Users begin by entering their measurement goals and current picture into the system, preferably via a Web site. The Visual Fitness Planner analyzes the user's data, and produces a customized fitness plan by applying a "morphing" process to the "before view". The picture is sectionalized into body components which are highly responsive to weight loss and components which are less responsive to weight loss, and the amount of change in each body section is determined by physiological tables and formulae. The resulting modified "after view" image is then returned to the user, preferably by online communications such as e-mail.

The Image Analyzer

The combination of three-dimensional ("3-D") morphing technology with mathematical statistics is used to project fat loss and muscle gain and to produce projected fitness outcomes. The user's input data includes skin fold, circumference, height, weight, BMR, and activity level. By entering the client's measurements into a mathematical formula, the user's picture can be morphed into the desired outcome. The combination of skin fold and circumference measurement produces an accurate morphing outcome for each user.

Business Method for Use of the Visual Fitness Planner

The Visual Fitness Planner helps the fitness industry overcome two of their biggest problems: obtaining new members and retaining current members. People may decide to join or renew their membership with a specific health club because they offer the Visual Fitness Planner as a service. By showing members how they will look 10 pounds thinner and giving them a clear-cut, understandable plan on how to achieve it, businesses in this industry will generate a satisfied and loyal clientele.

The Visual Fitness Planner is useful for nationwide health clubs, diet centers, and exercise equipment manufacturers. Direct marketing to Internet users may also be employed, as the technology and methods lend themselves well to interfacing to the user via common web site and browser technologies. As such, Internet users who are looking to start a fitness program will have access to the Visual Fitness Planner via the web site.

BRIEF DESCRIPTION OF THE DRAWINGS

The figures presented herein when taken in conjunction with the disclosure form a complete description of the invention.

DETAILED DESCRIPTION OF THE INVENTION

The Visual Fitness Planner is preferably an Internet-based fitness system and service, which helps the user meet his or her fitness objectives. However, it may be implemented as a stand-alone workstation for use within a health club facility or medical professional's office.

In general, users enter their measurements, goals and current picture into the system. The Visual Fitness Planner analyzes the user's data, generates a daily fitness program to help the customer reach his or her goal, and produces an after-fitness program image of the user. By setting the goals at an intermediate level, intermediate results can be projected and visualized The system employs readily available image morphing technology, driven by specialized technology to sectionalize the image into body components and predict specific size changes based upon physiological formulae and data tables.

System Overview

Figure 1:
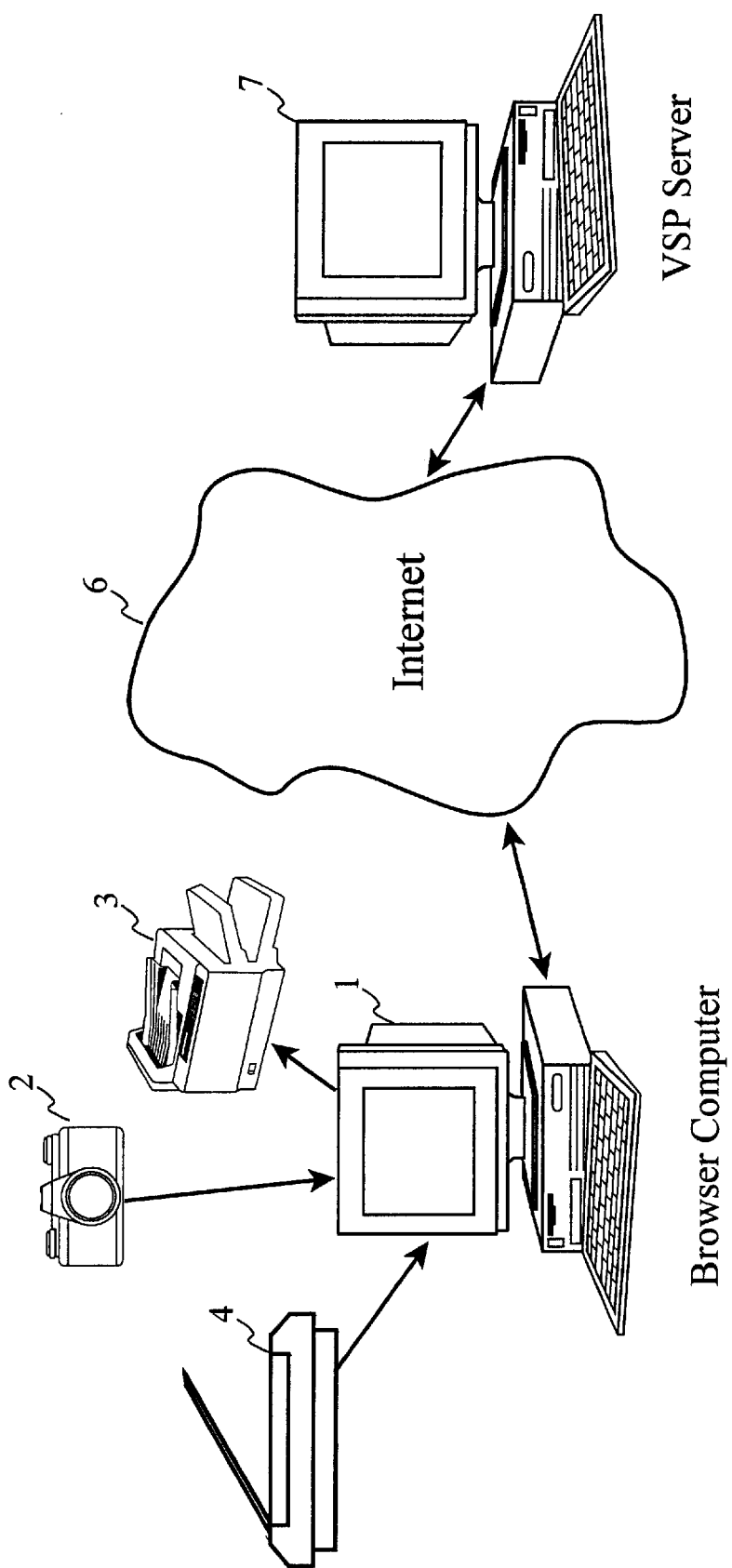
FIG. 1 shows the arrangement of an Internet browser computer, digital photography and scanning equipment, the Internet, and the Visual Fitness Planner server.

In the preferred embodiment, the user, health club advisor, or medical professional may use the system via a web site using a web browser, although in an alternate embodiment he or she may use the system directly. FIG. 1 illustrates the basic system components, including a browser computer (1) with Internet access (5), and a digital camera (2) or digital scanner (4), and optionally a printer (3). The computer can be any of several well-known and readily available systems, such as IBM-compatible personal computers running Microsoft's Windows operating system equipped with a web browser software such as Microsoft's Explorer or Netscape's Navigator, and appropriately equipped with a dial-up modem, cable modem, or Internet access via a local area network interface. Alternate computers, software and operating systems such as Apple iMac, Unix and Linux, may be used equally well.

The system also includes a computer network (6), such as the Internet or an intranet, and a Visual Fitness Planner ("VFP") server (7). This server is preferably based upon any of the well-known, readily available Internet web server platforms, such as an IBM-compatible personal computer running Microsoft's Windows NT operating system and an Apache web server. The user may point his or her web browser to the address or Universal Resource Locator ("URL") of the VFP server to access web pages and forms, such as HTML, XTML, and Common Gateway Interface ("CGI"), all of which are well-known within the art. The user may transfer his or her "before" photo in the form of any of many well-known digital photograph formats, such as Joint Photographic Experts Group ("JPEG"), bitmap ("BMP") or tagged-image file format ("TIFF") either by attachment to an e-mail message, retrieval by a Java client script (supplied by the VFP server), or by file transfer protocol ("FTP").

Figure 2:
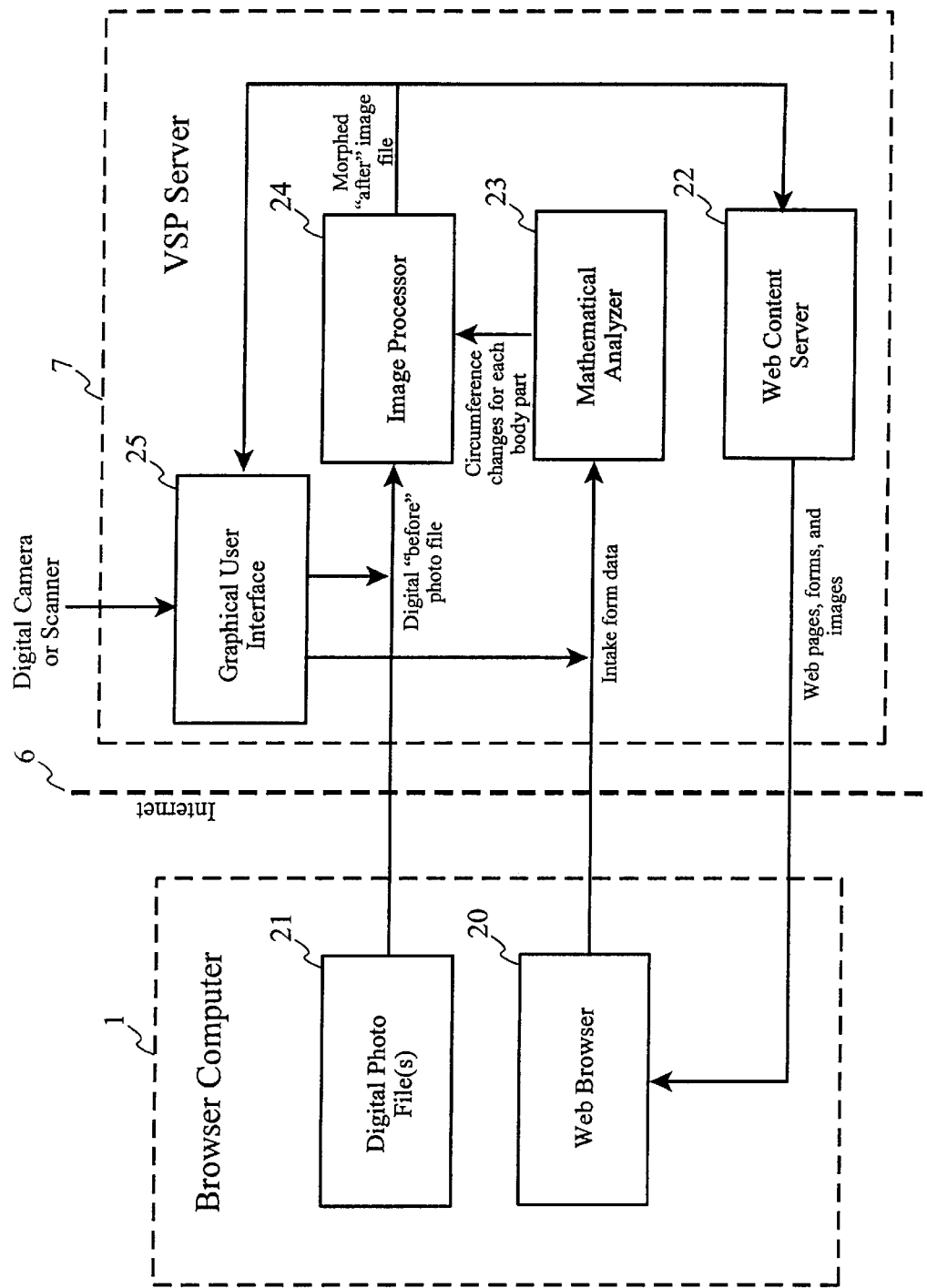
FIG. 2 illustrates in detail the functional organization of the Visual Fitness Planner server.

FIG. 2 shows the functional organization of the VFP server system (7), which includes a web content server (22), a mathematical analyzer (23) and an image processor (24). In the preferred embodiment, the VFP server system interfaces directly to the internet using any of the well-known methods, such as by modem or local area network The image processor (24) is described in more detail infra, as is the mathematical analyzer. If the system is implemented as a stand-alone workstation, it may also include a Graphical User Interface ("GUI") function for user control and input, such as a web browser software or custom GUI program. Additionally, for stand-alone use, a digital camera or scanner may be added to the system via a Universal Serial Bus ("USB") port, parallel port, or other common computer interface.

In the preferred embodiment, the user accesses the VFP planner (7) via an Internet (6) arrangement, using his or her browser computer (1). The web content server (22) transmits web pages, such as HTML and CGI forms, to the user to establish an account session and verify the user's identity, which are viewed and completed using a web browser (20). The user may then enter specific goals and measurement data, and submit a "before" photographic image file. The goals and measurements may be entered using a client-side Java applet, Adobe Acrobat Portable Document Format ("PDF"), or CGI form, and the photo file (21) may be uploaded to the VFP server by e-mail attachment, FTP, or a client-side script.

The user's measurements and goals are received by the mathematical analyzer (23), wherein certain formulae and data tables are applied to determine the amount of exercise to achieve the weight loss goal, and the amount of circumferential reduction in each body section.

The user's "before" image file (21) is received by the image processor (24), as are the body segment circumference changes from the mathematical analyzer (23). The image processor (24) segments the photo into body sections, applies the reduction changes by morphing the photo, and produces the "after" image, which is then returned to the user by the web content server (22) via a web page or e-mail attachment.

In the alternate, stand-alone embodiment, the "after" image is returned to the GUI (25) so that the operator and or client or patient may view the projected results.

In practice, the goals may be adjusted to produce the desired results and/or intermediate results, thereby providing a fill fitness plan needed to achieve the user's or client's goals.

Mathematical Analysis

The Visual Fitness Planner requires measurements to be taken in order to produce a customized fitness plan. The measurements needed include:

(1) The circumferences of the neck, arm, chest, waist, hips, thigh, and calf.

(2) The Skin fold of the neck, biceps, triceps, chest, scapula, abdomen, low back, high, thigh, hamstring, and calf.

(3) The user's height, weight, and age.

(4) Percent desired of fat.

By taking the skin fold and circumference measurements, the Visual Fitness Planner utilizes the following new formula to find the circumference of the fat layer and predict the reduction in circumference change for a particular body segment, all units are centimeters unless otherwise noted:

$$C_{change} = C_{after} - C_{before}$$

where $C_{change}$ is the change in circumference of a body part, $C_{after}$ is the final circumference of the body part after fat loss, and $C_{before}$ is the circumference of the body part at the beginning of the program.

Figure 3:
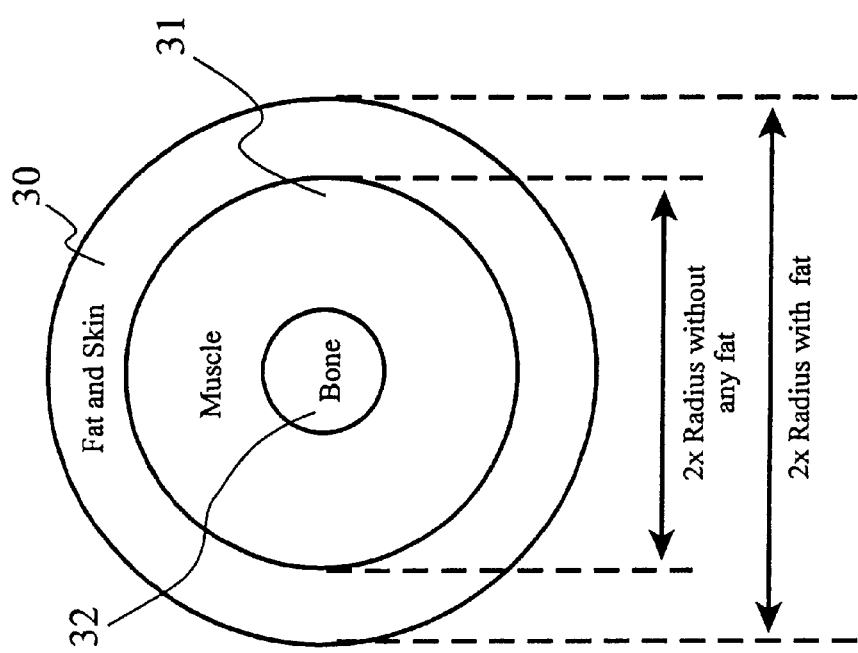
FIG. 3 depicts a cross-sectional view of a body portion to illustrate the calculation of base circumference of a body part.

FIG. 3 shows a cross sectional view of a body par, such as an upper arm or thigh, including a layer of fat with skin (30), a layer of muscle (31), and an underlying bone structure (32). The muscle and bone structure represent the component of the body part which will not be heavily affected by fat loss. Thus, the circumference of the body part without fat is calculated as:

$$\begin{aligned} C_{no\ fat} &= 2 \cdot \pi \cdot r_{no\ fat} \\ &= 2 \cdot \pi \cdot [r_{start} - \text{twice the depth of fat}] \\ &= 2 \cdot \pi \cdot [C_{before}/2\pi - (2 \cdot \text{skin\_fold\_measurement})] \end{aligned}$$

where $C_{no\ fat}$ represents the minimum circumference of a body part with no fat, $\pi$ represents an approximation the constant "pi", such as 3.14, $C_{before}$ represents the starting circumference (current circumference) of the body part, and "$skid_{13}$ fold_measurement" is the measurement of standard skin fold. All units are preferably in centimeters, although the formula holds for any unit of measure.

The body part circumference after a desired percentage fat loss is calculated:

$$\begin{aligned} C_{after} &= 2\pi \cdot \{r_{no\ fat} + \text{twice the desired depth of fat}\} \\ &\quad 2\pi \cdot \{[r_{start} - \text{twice the depth of fat}] + \\ &\qquad \text{twice the desired depth of fat}\} \\ &= 2\pi \cdot \{[C_{before}/2\pi - (2 \cdot \text{skin\_fold\_measurement})] + \\ &\qquad [2 \cdot \text{skin\_fold\_measurement} \cdot (1-P) \cdot V]\} \end{aligned}$$

where $C_{after}$ is the circumference of the body part after the desired fat loss, P is the amount of desired fat loss expressed in decimal form (i.e. 10% desired loss would be 0.10), and V is a constant based upon the body part being analyzed. The V constant is drawn from a table, and provides the variability to account for different body parts being more responsive to weight loss than others. For example, a body part which is highly responsive to weight loss would have a V value close to unity, while other less responsive body parts would have a greater than unity V value. TABLE 1 shows the preferred values for V.

TABLE 1

Adjustment Variable for Each Body Part

| Body Part | Skin Fold | Rank Order | Variable (V) |
|---|---|---|---|
| neck | 3 mm | 9 | 1 |
| biceps | 4 mm | 8 | 1.1 |
| triceps | 14 mm | 6 | 1.5 |
| chest | 21 mm | 5 | 1.8 |
| subscapula | 19 mm | 4 | 1.7 |
| abdomen | 30 mm | 1 | 2.5 |
| hip | 24 mm | 3 | 1.9 |
| thigh | 27 mm | 2 | 2.0 |
| calf | 13 mm | 7 | 1.2 |

The variable number is dependent on the skin fold of each body part. The rank order gives the ability to place the skin fold measurements in an order that the variable members can be assigned By ranking the ski fold measurements from greatest to least the variable numbers can be assigned. This table can change depending on where a person stores their fat.

Method of Producing the Predicted Image

In the preferred embodiment, the following method is implemented in software. The programming language is of little consequence, as the required calculations can be performed by most well-known languages, including "C", Java, and "C++". The method comprises the steps of:

(a) Receive from intake data sheet all user information needed for analysis (ie. skin fold measurements, age, height, weight, desired loss amount), and receive "before" photographic image file.

(b) Scale real-life measurements to picture size.

(c) Place photograph on grid.

(d) Convert intake data to reduction on photograph utilizing formula (e) Place locating grids of individual body parts on "before" image.

(f) Find outline of the individual body parts within locating grids.

(g) Apply reduction of the individual body parts using morphing function.

(h) Applying original "before" photo next to reduced "after" photo.

In the first step, receipt of data from intake data sheet, the software receives the user's name, age, current weight, height, and circumference measurements for the neck, arm chest, abdomen, hips, thigh, and calf The data also includes skin fold measurements for the neck, biceps, triceps, chest, subscap, abdomens, hips, thigh, and calf The data further includes the desired percent body fat goal.

In the second step, the measurements are scaled to the picture size by talking the person's height and dividing by picture height. Then, this ratio is multiplied by all other real life measurements to produce scaled measurements. For example, if a person is actually 5 feet 9 inches (69 inches), and the photograph submitted represents a 7 inch tall image, the scaling ratio is 69/7=9.8. So, all real-life measurements would be multiplied by the inverse of the scaling ratio to yield a scaled measurement set.

Figure 4:
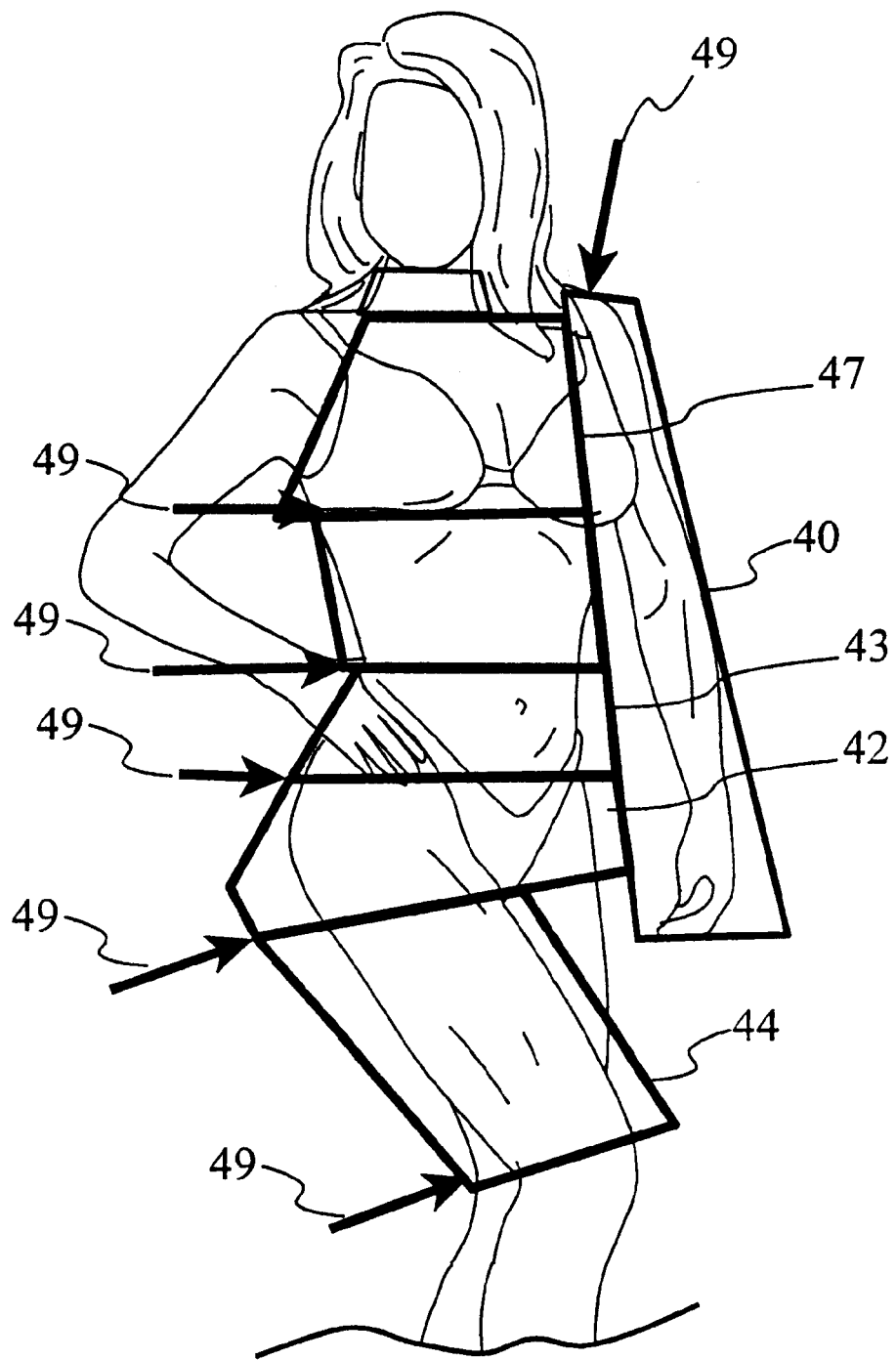
FIG. 4 sets forth an example of locating grids placed on a subject's photograph to aid the image processor in locating each body part.

In the third step, a locating grid is used to identify each body part, as shown in FIG. 4. Locating grids are placed on the arms (40), hips and/or buttocks (42), abdomen (43), thigh (44), calf (45), chest (47), and neck (46). In the preferred embodiment, a feature extraction algorithm may be used to automatically find each body portion, aided by the placement of arrows (49) on a background behind the subject at the time of taking the photograph. Alternatively, the body-part identifying grids may be placed on the photo manually through a graphical user interface. Both implementations are within the skill of the art of software engineers with expertise in this type of image processing.

Figure 5:
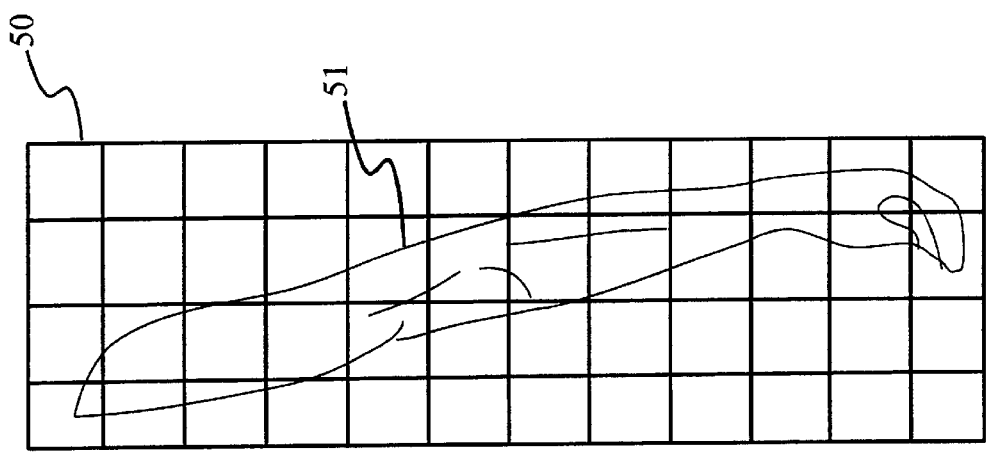
FIG. 5 shows the result of the placing of a grid over a single body part during the process of finding edges of the body part.

In the fourth step, a grid is overlaid on each body segment image, as shown in FIG. 5. The grid (50) is useful in the process in finding the edges (51) of the image of the body part, and in applying a percent reduction to the image.

Figure 6:
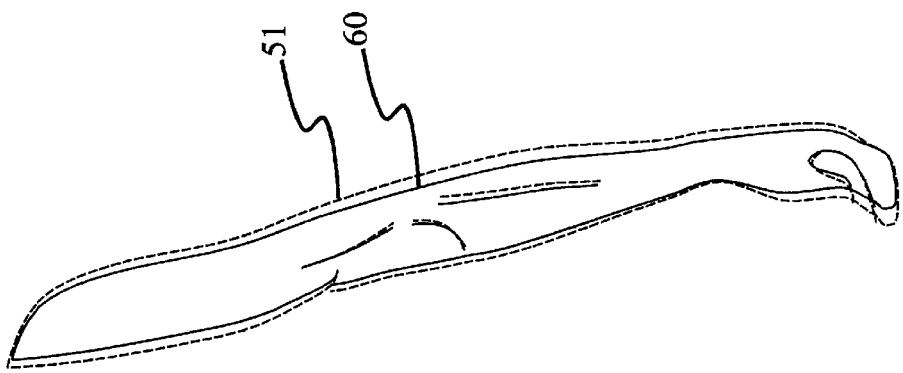
FIG. 6 illustrates the result of the morphing to reduce the width of the body part image.

In the fifth step, the reductions for each body segment are applied using an image morphing function, as shown in FIG. 6 with the new edges (60) of the body part image. This yields an "after" image in which each body part has been analytically reduced based upon each part's responsiveness to fat loss, the estimated beginning fat layer thickness based upon the skin fold measurements, and the desired amount of reduction of fat.

Figure 7:
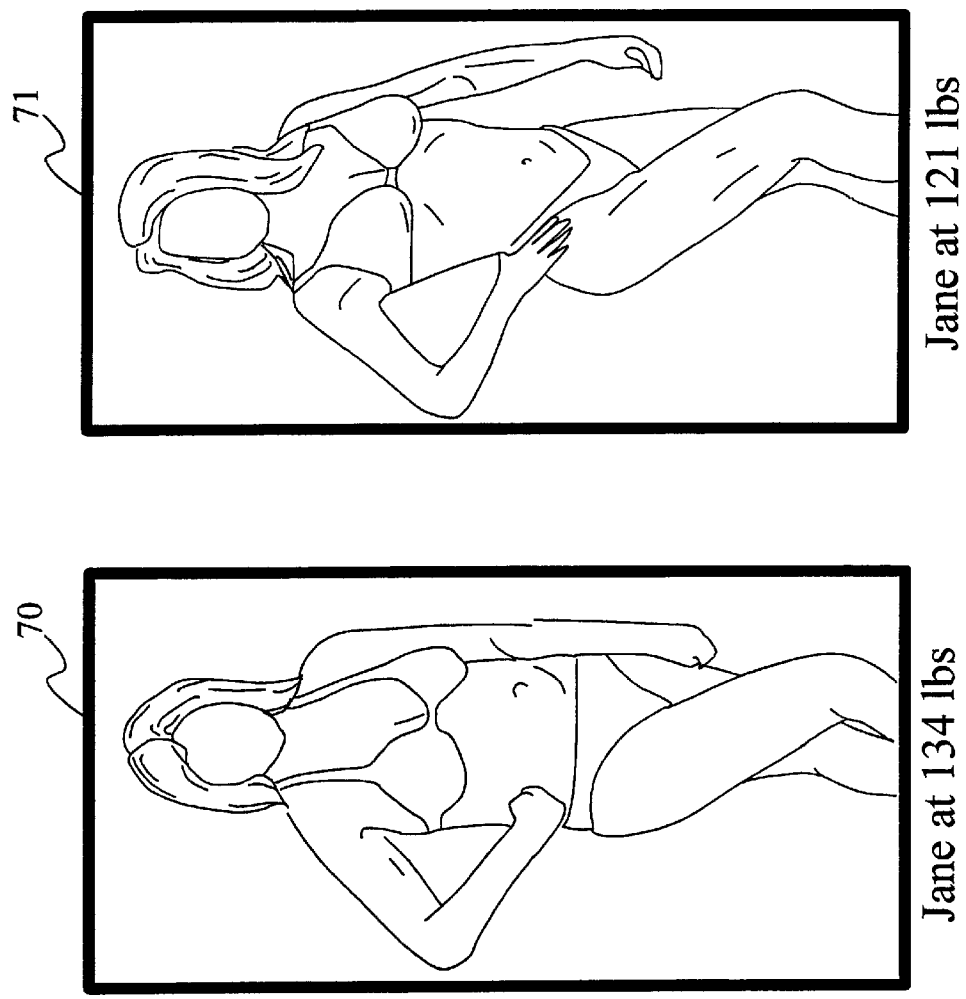
FIG. 7 shows a simulated side-by-side "before" and "after" comparison output from the system.

Finally, simulated "before" (70) and "after" (71) images are displayed side-by-side for ease of comparison, such as shown in FIG. 7. Thus, a more accurate system and method are provided which scales the current image of the client or patient on a segmented basis using physiological calculations.

While the disclosure contained herein has set forth a preferred embodiment of the invention, and the fundamental components used within the invention are well known within the art, it will be appreciated by those who are skilled in the art that variations to the combination of elements and steps disclosed can be made without departing from the scope and spirit of the invention.

What is claimed is:

1. A method for producing an image predictive of a person's appearance resulting from following a weight loss and training regimen, said method comprising the steps of:
   receiving a first image of a person in a pre-regimen condition;
   receiving a first data set of body measurements for said person;
   receiving a second data set indicating at least one goal for results of said regimen;
   separating said first image into a plurality of body segment images;
   modifying each body segment image based upon said second data set and said first data set in a manner relevant to predictable weight loss in each body segment by morphing each body segment based upon predictable fat loss in each body segment;
   reconstructing a full-body image by combining said modified body segment images to produce a second digital photograph, said second digital photograph representing a predicted appearance of said person following said regimen.

2. A method for producing an image predictive of a person's appearance as set forth in claim 1 wherein said step of receiving a first data set of body measurements further comprises receiving a weight measurement for said person.

3. A method for producing an image predictive of a person's appearance as set forth in claim 1 wherein said step of receiving a first data set of body measurements further comprises receiving at least one body fat measurement.

4. A method for producing an image predictive of a person's appearance as set forth in claim 3 wherein said step of receiving at least one body fat measurement includes receiving a skin fold measurement taken at the person's neck.

5. A method for producing an image predictive of a person's appearance as set forth in claim 3 wherein said step of receiving at least one body fat measurement includes receiving a skin fold measurement taken at the person's biceps.

6. A method for producing an image predictive of a person's appearance as set forth in claim 3 wherein said step of receiving at least one body fat measurement includes receiving a skin fold measurement taken at the person's triceps.

7. A method for producing an image predictive of a person's appearance as set forth in claim 3 wherein said step of receiving at least one body fat measurement includes receiving a skin fold measurement taken at the person's chest.

8. A method for producing an image predictive of a person's appearance as set forth in claim 3 wherein said step of receiving at least one body fat measurement includes receiving a skin fold measurement taken at the person's subscapula.

9. A method for producing an image predictive of a person's appearance as set forth in claim 3 wherein said step of receiving at least one body fat measurement includes receiving a skin fold measurement taken at the person's abdomen.

10. A method for producing an image predictive of a person's appearance as set forth in claim 3 wherein said step of receiving at least one body fat measurement includes receiving a skin fold measurement taken at the person's hip.

11. A method for producing an image predictive of a person's appearance as set forth in claim 3 wherein said step of receiving at least one body fat measurement includes receiving a skin fold measurement taken at the preson's thigh.

12. A method for producing an image predictive of a person's appearance as set forth in claim 3 wherein said step of receiving at least one body fat measurement includes receiving a skin fold measurement taken at the person's calf.

13. A method for producing an image predictive of a person's appearance as set forth in claim 1 wherein said step of receiving a second data set indicating at least one goal for results comprises receiving a target weight value.

14. A method for producing an image predictive of a person's appearance as set forth in claim 1 wherein said step of receiving a second data set indicating at least one goal for results comprises receiving a target body fat value.

15. A method for producing an image predictive of a person's appearance as set forth in claim 1 wherein said step of modifying each body segment image comprises the steps of:
  determining a fat layer thickness surrounding each body segment based upon said first data set and a third data set of values for each body segment:
  determining a reduced fat layer thickness surrounding each body segment based upon predicted fat loss in each body segment;
  determining a final body segment size based upon said first data set and said reduced fat layer thickness for each body segment.

16. A system for producing images predictive of a person's appearance resulting from following a weight loss and training regimen, said system comprising:
  a computing platform capable of executing application software, said platform including
    a processor, computer-readable memory and persistent data storage,
    an image input device, and an image output device; and
  a computer program product disposed in a computer readable media for receiving an image of a person receiving a first set of data values representing current measurements for said person, receiving a second set of data values representing at least one goal measurement, and a predictive analysis function for applying a third set of data values to each body segment of said digital photograph image so as to create a predictive image of said person based upon said current measurements by morphing each body segment based upon predictable fat loss in each body segment, said predictive image being available via said image output device.

17. A system for producing images predictive of a person's appearance as set forth in claim 16 wherein said output device is a computer monitor.

18. A system for producing images predictive of a person's appearance as set forth in claim 16 wherein said output device is a printer device.

19. A system for producing images predictive of a person's appearance as set forth in claim 16 wherein said input device is a digital camera.

20. A system for producing images predictive of a person's appearance as set forth in claim 16 wherein said input device is a scanner.

21. A system for producing images predictive of a person's appearance as set forth in claim 16 further comprising a computer network interface including communications protocol suitable for client-server communications, and suitable for receiving said first and second data sets and said digital photograph input.

22. A system for producing images predictive of a person's appearance as set forth in claim 21 wherein said output device comprises a computer display on a client computer interconnected via a computer network.

23. A system for producing images predictive of a person's appearance as set forth in claim 21 wherein said output device comprises a client computer printer device interconnected via a computer network.

24. A system for producing images predictive of a person's appearance as set forth in claim 21 wherein said computer network interface further comprises an Internet interface.

25. A system for producing images predictive of a person's appearance as set forth in claim 21 wherein said computer network interface further comprises an electronic mail server interface and communications protocol.

26. A method for attracting and retaining clients and members of health and fitness services such as weight loss clinics, packaged food distributors, and fitness centers, comprising the steps of:
  providing a system with a client interface;
  receiving an image of a client, a set of client measurements and at least one goal measurement;
  segmenting said client image into a plurality of body segment images;
  modifying each body segment image by morphing each body segment based upon predictable fat loss in each body segment to represent a predictive image of each body segment,
  providing a predictive image comprised of the modified body segment images, thereby allowing said client to visualize actual results attainable through a regimen of diet and exercise based upon actual body measurements and regimen goals.

27. A method for attracting and retaining clients and members as set forth in claim 26 wherein said set step of providing a system with a client interface comprises providing a client interface accessible and operable by an Internet browser computer via an Internet.

28. A method for attracting and retaining clients and members as set forth in claim 26 wherein said step of providing a predictive image comprises providing a predictive image file to an Internet browser computer via an Internet.

29. A method for attracting and retaining clients and members as set forth in claim 26 wherein said step receiving a set of client measurements comprises receiving at least one fat measurement.

30. A method for attracting and retaining clients and members as set forth in claim 29 wherein said step receiving at least one fat measurement comprises receiving a skin fold measurement.

* * * * *